United States Patent
McPeak

(10) Patent No.: US 9,814,401 B2
(45) Date of Patent: Nov. 14, 2017

(54) ANGIOSOME-BASED PERFUSION MONITORING SYSTEM

(71) Applicant: Covidien LP, Mansfield, MA (US)

(72) Inventor: Thomas McPeak, Shakopee, MN (US)

(73) Assignee: Covidien LP, Mansfield, MA (US)

( * ) Notice: Subject to any disclaimer, the term of this patent is extended or adjusted under 35 U.S.C. 154(b) by 1038 days.

(21) Appl. No.: 13/928,665

(22) Filed: Jun. 27, 2013

(65) Prior Publication Data

US 2014/0012108 A1    Jan. 9, 2014

Related U.S. Application Data

(60) Provisional application No. 61/668,479, filed on Jul. 6, 2012.

(51) Int. Cl.
*A61B 5/026* (2006.01)
*A61B 5/0295* (2006.01)
(Continued)

(52) U.S. Cl.
CPC .......... *A61B 5/0295* (2013.01); *A61B 5/0205* (2013.01); *A61B 5/02007* (2013.01);
(Continued)

(58) Field of Classification Search
USPC ................. 600/363, 468, 465, 504
See application file for complete search history.

(56) References Cited

U.S. PATENT DOCUMENTS

| | | | |
|---|---|---|---|
| 7,354,410 B2 * | 4/2008 | Perry | A61H 9/0078 128/DIG. 20 |
| 7,736,311 B2 | 6/2010 | Bartnik et al. | |

(Continued)

FOREIGN PATENT DOCUMENTS

| | | |
|---|---|---|
| CN | 1080510 A | 1/1994 |
| WO | 2005067387 A2 | 7/2005 |

(Continued)

OTHER PUBLICATIONS

Office action with English translation for Russian Application No. 2013130168/14, dated Mar. 3, 2015, 8 pages.
(Continued)

*Primary Examiner* — Jacqueline Cheng
*Assistant Examiner* — Jairo Portillo

(57) ABSTRACT

A compression device includes at least one pressurizable bladder to substantially occlude blood flow into skin capillary beds adjacent to the at least one pressurizable bladder, and a plurality of perfusion sensors. In operation a first-angiosome sensor detects the perfusion parameter of a skin capillary bed in a first angiosome of the limb, and a second-angiosome sensor detects the perfusion parameter of a skin capillary bed in a second angiosome of the limb that is different from the first angiosome. A control circuit maps sensor signals from the first-angiosome sensor to the first angiosome or a first artery of the limb, and maps sensor signals from the second-angiosome sensor to the second angiosome or a second artery of the limb different from the first artery of the limb. For each perfusion sensor, the control circuit determines whether the received sensor signals are indicative of peripheral artery disease.

27 Claims, 12 Drawing Sheets

(51) Int. Cl.
*A61B 5/0205* (2006.01)
*A61B 5/02* (2006.01)
*A61B 5/1455* (2006.01)
*A61B 5/00* (2006.01)

(52) U.S. Cl.
CPC ......... *A61B 5/0261* (2013.01); *A61B 5/14551* (2013.01); *A61B 5/7246* (2013.01); *A61B 5/7282* (2013.01)

(56) References Cited

U.S. PATENT DOCUMENTS

| | | | |
|---|---|---|---|
| 2002/0087089 A1* | 7/2002 | Ben-Haim | A61B 5/02014 600/509 |
| 2007/0066897 A1* | 3/2007 | Sekins | A61B 5/445 600/437 |
| 2007/0225606 A1 | 9/2007 | Naghavi et al. | |
| 2008/0183059 A1 | 7/2008 | LaPlante et al. | |
| 2008/0208011 A1* | 8/2008 | Shuler | A61B 5/0215 600/301 |
| 2009/0124913 A1* | 5/2009 | Yamashita | A61B 5/02141 600/499 |
| 2009/0281412 A1 | 11/2009 | Boyden et al. | |
| 2010/0030034 A1* | 2/2010 | Schulhauser | A61B 5/0205 600/301 |
| 2010/0198062 A1 | 8/2010 | Everett et al. | |
| 2011/0224589 A1* | 9/2011 | Bock | A61H 9/0078 601/152 |
| 2013/0184745 A1* | 7/2013 | Leschinsky | A61B 5/6831 606/202 |

FOREIGN PATENT DOCUMENTS

| | | |
|---|---|---|
| WO | 2007030379 A2 | 3/2007 |
| WO | 2008044822 A1 | 4/2008 |

OTHER PUBLICATIONS

Chinese Notification of the First Office action with English translation for Application No. 201310451777.5, dated Oct. 10, 2014, 10 pages.
L Tudhope, Diabetic Foot Ulcers—The Importance of Angiosomes in Healing Foot Ulcers, Wound Healing Southern Africa 2008 vol. 1 No. 2, pp. 13-14.
Japanese Notice of Reasons for Rejection for Application No. 2013-141666, dated Jul. 1, 2014, 7 pages, Japan.
Patent Examination Report No. 1 for Australian Application No. 2013206663 dated Jun. 27, 2014, 3 pages, Woden, Australia.
Notice of Preliminary Rejection for Korean Application No. 10-2013-79058 with English translation dated Jul. 21, 2014, 4 pages, Korea.
Hiroo Suami, M.D., et al., Angiosome Territories of the Nerves of the Lower Limbs, Jack Brockhoff Reconstructive Plastic Surgery Research Unit, Royal Melbourne Hospital, and the Department of Anatomy and Cell Biology, University of Melbourne, Jan. 13, 2003, 9 pages, Melbourne, Australia.
European Search Report for Application No. EP13174271.0 dated Oct. 8, 2013, 7 pages, Berlin, Germany.
Office action with for Canadian Application No. 2,819,803, dated Feb. 17, 2015, 4 pages.
Examination Report from counterpart European Application No. 13174271.0, dated Mar. 8, 2017, 5 pages.

* cited by examiner

ANGIOSOME-BASED PERFUSION MONITORING SYSTEM

CROSS-REFERENCE TO RELATED APPLICATIONS

The present application claims priority to U.S. Provisional Application Ser. No. 61/668,479, filed Jul. 6, 2012, the entirety of which is hereby incorporated by reference.

FIELD OF THE DISCLOSURE

The present invention generally relates to an angiosome-based monitoring system.

BACKGROUND

In 1987, Taylor and Palmer introduced the angiosome concept, in which the body is considered to consist of three-dimensional blocks of tissue supplied by particular source arteries. FIG. 9 is a schematic, anterior diagram of the lower body depicting angiosomes, and FIG. 10 schematically illustrates the source arteries associated with the angiosomes in FIG. 9. The source arteries associated with respective angiosomes include the deep circumflex iliac artery (101), common femoral artery (102), lateral circumflex femoral artery (103), superficial femoral artery (104), medial circumflex femoral artery (105), and descending genicular artery (106). FIG. 11 is a schematic, posterior diagram of the lower body depicting angiosomes, and FIG. 12 schematically illustrates the source arteries associated with the angiosomes in FIG. 11. The source arteries associated with respective angiosomes include the lumbar artery (107), superior gluteal artery (108), inferior gluteal artery (109), internal pudendal artery (110), deep femoral artery (111), popliteal artery (112), posterior tibial artery (113), peroneal artery (114), anterior tibial artery (115), lateral plantar artery (116), medial plantar artery (117), and sural artery (118).

SUMMARY

In one aspect a compression device is sized and shaped for placement on a limb of a subject. The compression device includes at least one pressurizable bladder configured to exert a suitable compressive force on the limb of the subject when pressurized to substantially occlude blood flow into skin capillary beds adjacent to the at least one pressurizable bladder, and a plurality of perfusion sensors. In operation at least one sensor of the plurality of perfusion sensors is a first-angiosome sensor for detecting the perfusion parameter of a skin capillary bed in a first angiosome of the limb, and at least one sensor of the plurality of perfusion sensors is a second-angiosome sensor for detecting the perfusion parameter of a skin capillary bed in a second angiosome of the limb that is different from the first angiosome. A control circuit receives separate sensor signals from the plurality of perfusion sensors on the compression device during depressurization of the at least one bladder, wherein the sensor signals are indicative of perfusion parameters of skin capillary beds adjacent the perfusion sensors for quantifying skin capillary bed perfusion. The control circuit maps sensor signals from the first-angiosome sensor to at least one of the first angiosome and a first artery of the limb, and maps sensor signals from the second-angiosome sensor to at least one of the second angiosome and a second artery of the limb different from the first artery of the limb. For each perfusion sensor, the control circuit determines whether the received sensor signals are indicative of peripheral artery disease.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
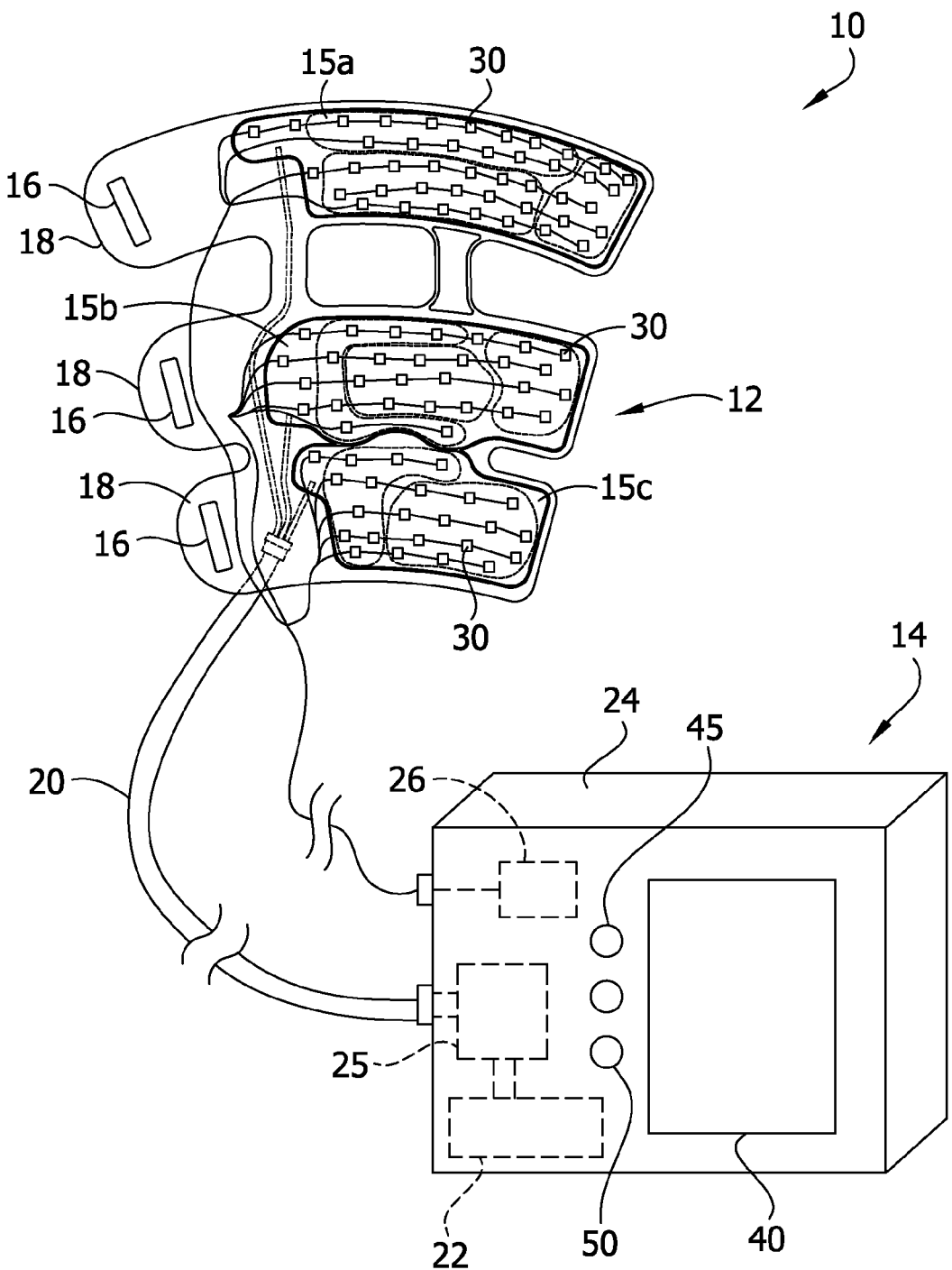
FIG. 1 is a schematic representation of one embodiment of an angiosome-based perfusion monitoring system, the monitoring system including a compression device and a control device.
Figure 2:
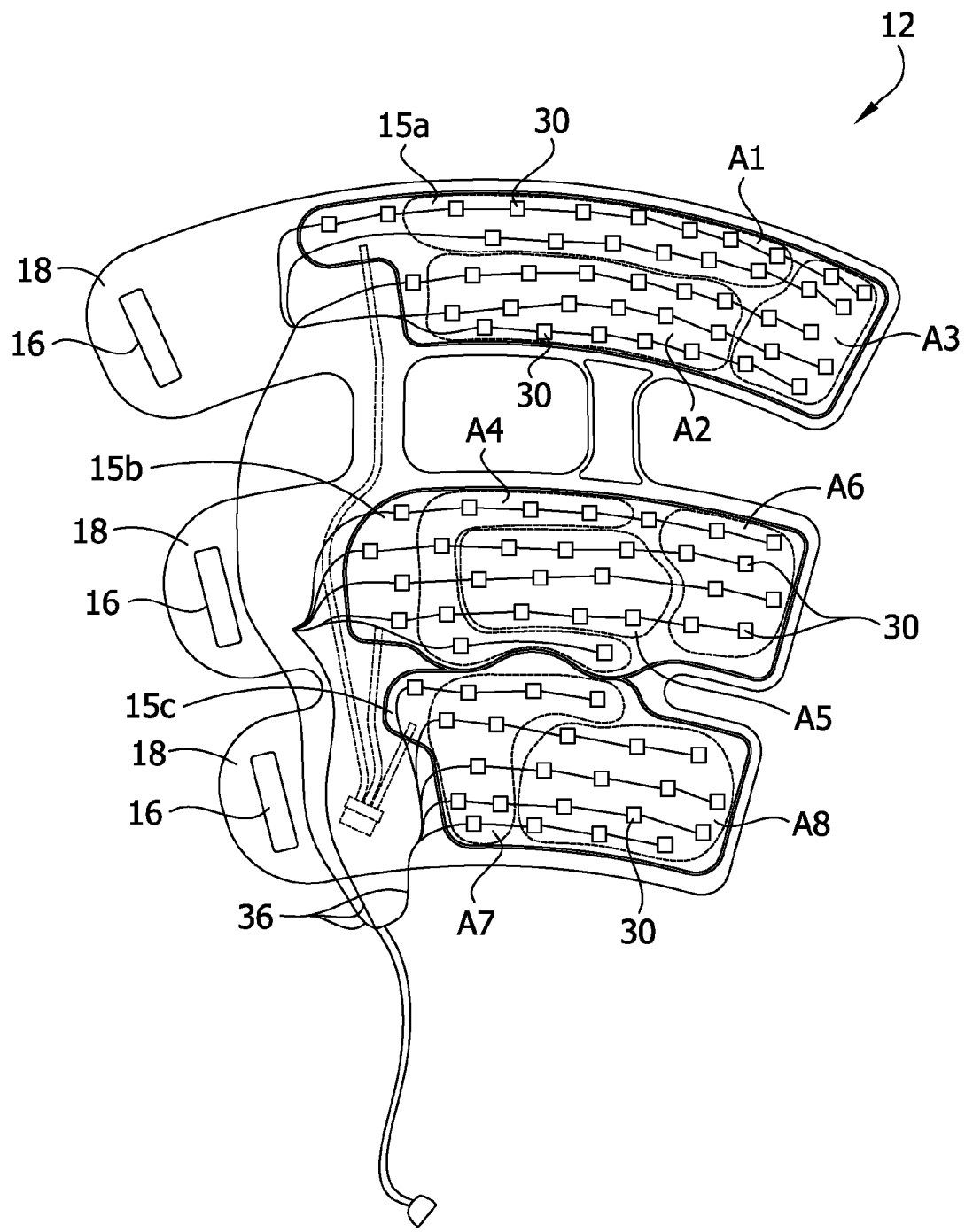
FIG. 2 is an inner side view of the compression device of FIG. 1, including markings to indicated groupings of perfusion sensors according to angiosomes of the leg.
Figure 3:
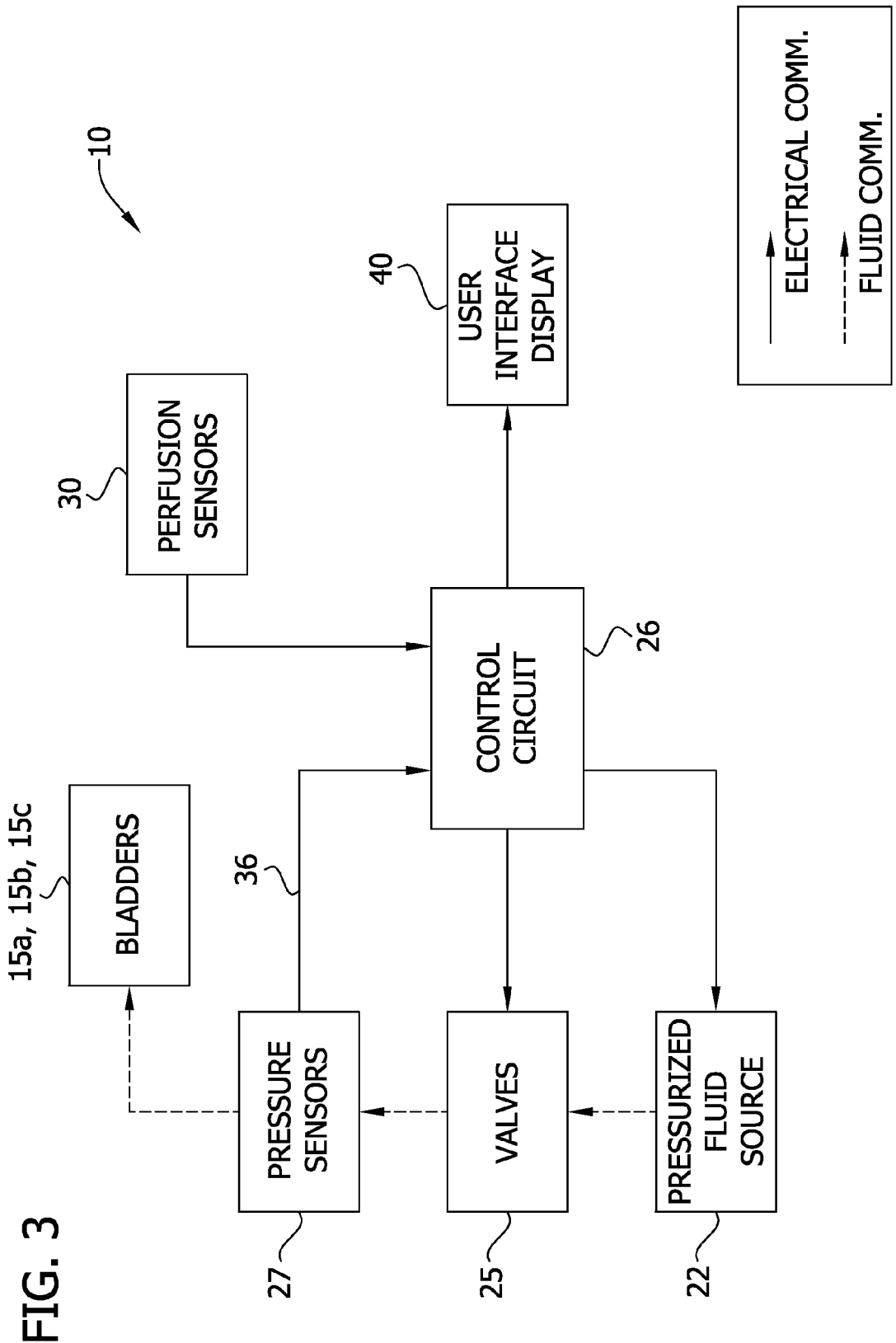
FIG. 3 is a diagram of the angiosome-based perfusion monitoring system, including electrical and fluid communications between components thereof.
Figure 4:
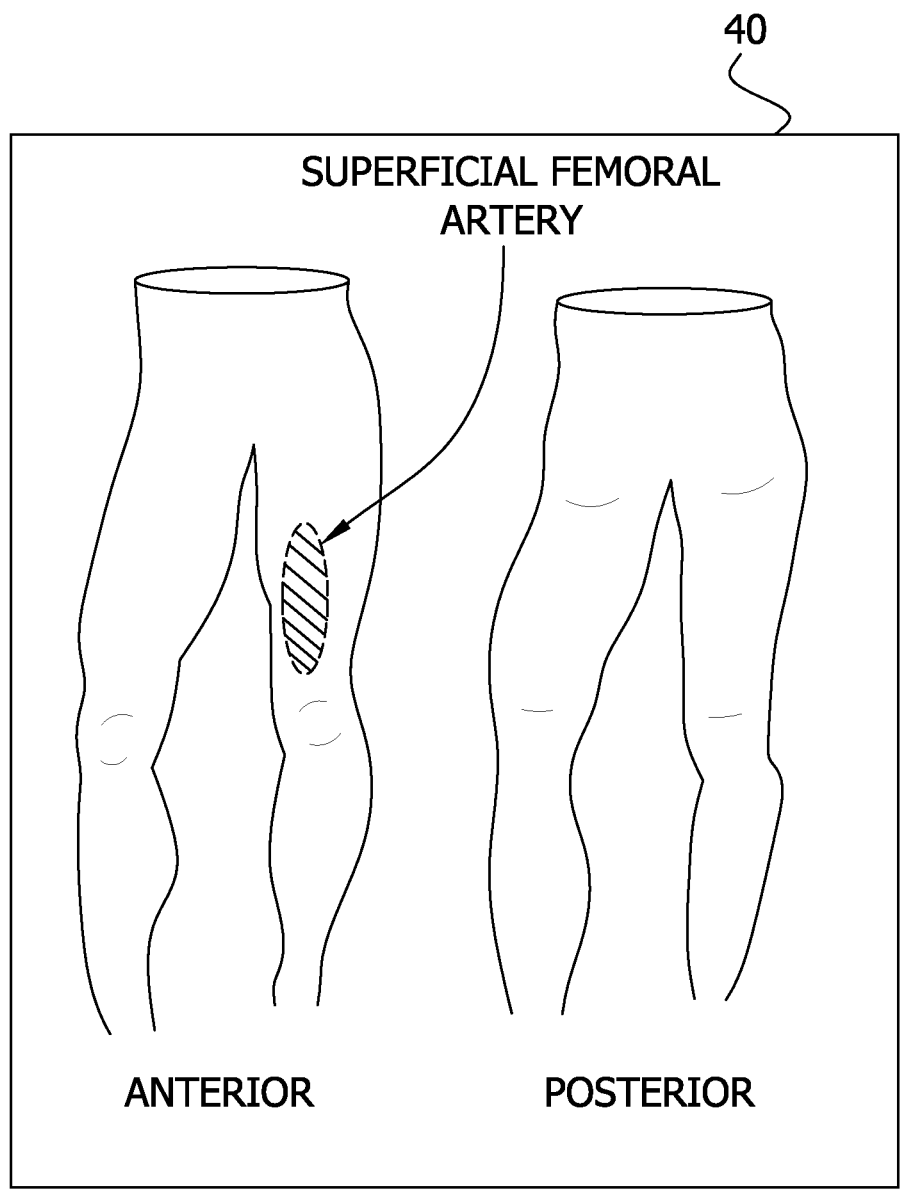
FIG. 4 is an exemplary, schematic screen shot of a graphical user interface during a first mode of operation of the monitoring system.

Referring to FIGS. 1-3, an angiosome-based perfusion monitoring system for treating and/or diagnosing peripheral artery disease is indicated generally at reference numeral 10. The angiosome-based perfusion monitoring system 10 includes a compression device, generally indicated at 12, and a control device, generally indicated at 14. The illustrated compression device 12 is configured to be disposed around a leg of a wearer. In particular, the illustrated compression device 12 is configured to be wrapped around the leg of the wearer and extend longitudinally from the wearer's thigh toward the wearer's ankle (e.g., including the calf), although the compression device may be configured to be wrapped around only a portion of the wearer's leg (e.g., the wearer's calf). The compression device 12 includes one or more inflatable bladders, and in the illustrated embodiment, the compression device includes three longitudinally-spaced bladders: a thigh bladder 15a, a calf bladder 15b, and an ankle bladder 15c. Each bladder 15a, 15b, 15c is sized and shaped for wrapping around a substantially full circumference of the wearer's leg, although the bladders may be configured to wrap partially around the circumference of the wearer's leg. It is understood that in other embodiments the compressive device 12 may include a single bladder or any number of bladders. It is also understood that in other embodiments the compression device may be configured to be wrapped around other parts of the wearer's body, including but not limited to one or more toes, one or more fingers, one or more feet, one or more hands, and one or more arms.

The compression device 12 includes fasteners 16 (e.g., hook and loop fasteners) for securing the compression device to the wearer's leg. For example, in the illustrated embodiment, the fasteners 16 comprise male or hook fasteners that are secured to the inner side of securement flaps 18 of the compression sleeve. The compression sleeve 12 is wrapped around the wearer's leg such that the back side (i.e., posterior side) of the leg is laid on the inner side of the compression sleeve. The right flaps (as taken from the viewpoint of FIG. 1) are wrapped over the front side (i.e., anterior side) of the wearer's leg, and then the left flaps are wrapped over the right flaps and the hook fasteners 16 are secured to female or loop fasteners on the outer surface of the compression sleeve. The compression device 12 may comprise a pair of opposing, sheets of generally fluid-impermeable material. These sheets may be heat welded together to form the bladders 15a, 15b, 15c. Also, in one embodiment the compression device 12 may be radiolucent to allow for angiographic procedures. In general, the compression device 12 may be substantially similar to inflatable compression sleeves used in prevention of deep vein thrombosis.

Referring to FIG. 1, each of the bladders 15a, 15b, 15c is fluidly connected to the control device 14 via flexible tubing 20 (e.g., three tubes) for selectively inflating the bladders to a selected pressure and deflating the bladders. The control device 14 includes a fluid compressor 22, located inside a housing 24 of the control device, for delivering pressurized fluid (e.g., air) to the bladders 15a, 15b, 15c. A control circuit 26 in the control device housing 24 is programmed to control the inflation and deflation of the bladder 15a, 15b, 15c. For example, the control circuit 26 may be in electrical communication with the fluid compressor 22 and/or valves 25 (e.g., solenoids) in the control device housing 14 for regulating introduction of pressurized fluid from the fluid compressor into the tubing 20. The control circuit 26 is also in electrical communication with one or more pressure sensors 27 (FIG. 3) that detect or indicate the pressure in the bladders 15a, 15b, 15c and communicate such information to the control circuit. For reasons explained in more detail below, in one embodiment the control circuit 26 is programmed (broadly, "configured") to pressurize (e.g., inflate) the bladders 15a, 15b, 15c to pressures from about 3 psi to about 5 psi for a predetermined amount of time to substantially occlude blood flow into skin capillary beds of the leg adjacent the bladders when the compression device 12 is donned by a wearer (e.g., a patient).

Referring still to FIGS. 1 and 2, the compression device 12 also includes a plurality of perfusion sensors 30 for use in detecting the microcirculatory flow of blood (or perfusion) within skin capillary beds of the leg. In one non-limiting example, the perfusion sensors 30 comprise pulse oximetry sensors, which illuminate the skin and measure changes in light absorption, the function of which for detecting microcirculatory flow of blood is generally known in the art. The perfusion sensors 30 may be of other types for use in detecting microcirculatory flow. For example, other ways of measuring microcirculatory flow include ultrasound; optical plethysmography; sound, e.g. a microphone for pulsatile flow in the macrocirculation; metabolic indicators such as pCO2 or lactate; and bioimpedance.

In the illustrated embodiment, the perfusion sensors 30 are secured adjacent to the inner side of the compression device 12. The sensors 30 are arranged in rows extending across each of the bladders 15a, 15b, 15c, although it is understood that the sensors may be in other arrangements. Each row includes a plurality of spaced apart sensors 30 that are electrically connected to the control device 12 via one or more cables or wires 36 leading to the control device 14. The sensors 30 send individual sensor signals to the control circuit 26, each sensor signal being indicative of the microcirculatory flow of blood (or perfusion) within skin capillary beds of the leg. The sensors 30 are located on the compression device 12 such that each sensor measures the microcirculatory flow of blood (or perfusion) in skin capillary beds within one or more angiosomes of the leg. As explained in more detail below, the control circuit 26 is programmed to map or relate the signal from each sensor 30 to the artery of the leg that corresponds to the angiosome being monitored by the sensor. The number of sensors 30 on the compression device 12 may vary, although it is preferred (though not mandatory) that each identified angiosome is monitored by at least one sensor. In the illustrated embodiment, each identified angiosome is monitored by a plurality of sensors 30. Moreover, the illustrated compression device 12 is suitable for use on a right leg of a patient. It is envisioned that the compression device 12 would be limb specific. However, a universal compression device operable on either leg falls within the scope of the present invention.

In one mode of operation (e.g., a diagnostic mode), the control device 14 is configured to not only determine if there is possible arterial stenosis in the leg being diagnosed, but also identify the artery that is likely occluded. In one example, the control circuit 26 is programmed to inflate (i.e., pressurize) the bladders 15a, 15b, 15c to a suitable pressure (e.g., 4 psi) for a predetermined amount of time (e.g., 10-20 seconds) to substantially occlude the flow of blood into the capillary beds in the skin of the leg adjacent the bladders. For example, the control circuit 26 may activate the compressor 22 and open the valves 25 to allow pressurized air to flow into the bladders 15a, 15b, 15c. The control circuit 26 receives pressure signals from pressure sensors (not shown) near the valves 25, which are indicative of the pressure in the respective bladders 15a, 15b, 15c. When a predetermined, threshold pressure has been reached, the control circuit 26 may actuate closing of the valves 25 to maintain the pressure in the bladders 15a, 15b, 15c. In another embodiment, the control circuit 26 may receive sensor signals from the sensors 30 as the bladders 15a, 15b, 15c are being pressurized. In such an embodiment, the control circuit 26 may be programmed to pressurize the bladders 15a, 15b, 15c until the microcirculatory flow in the capillary beds has reached a threshold value, which indicates that the bladder is occluding blood flow to the capillary beds.

Figure 8:
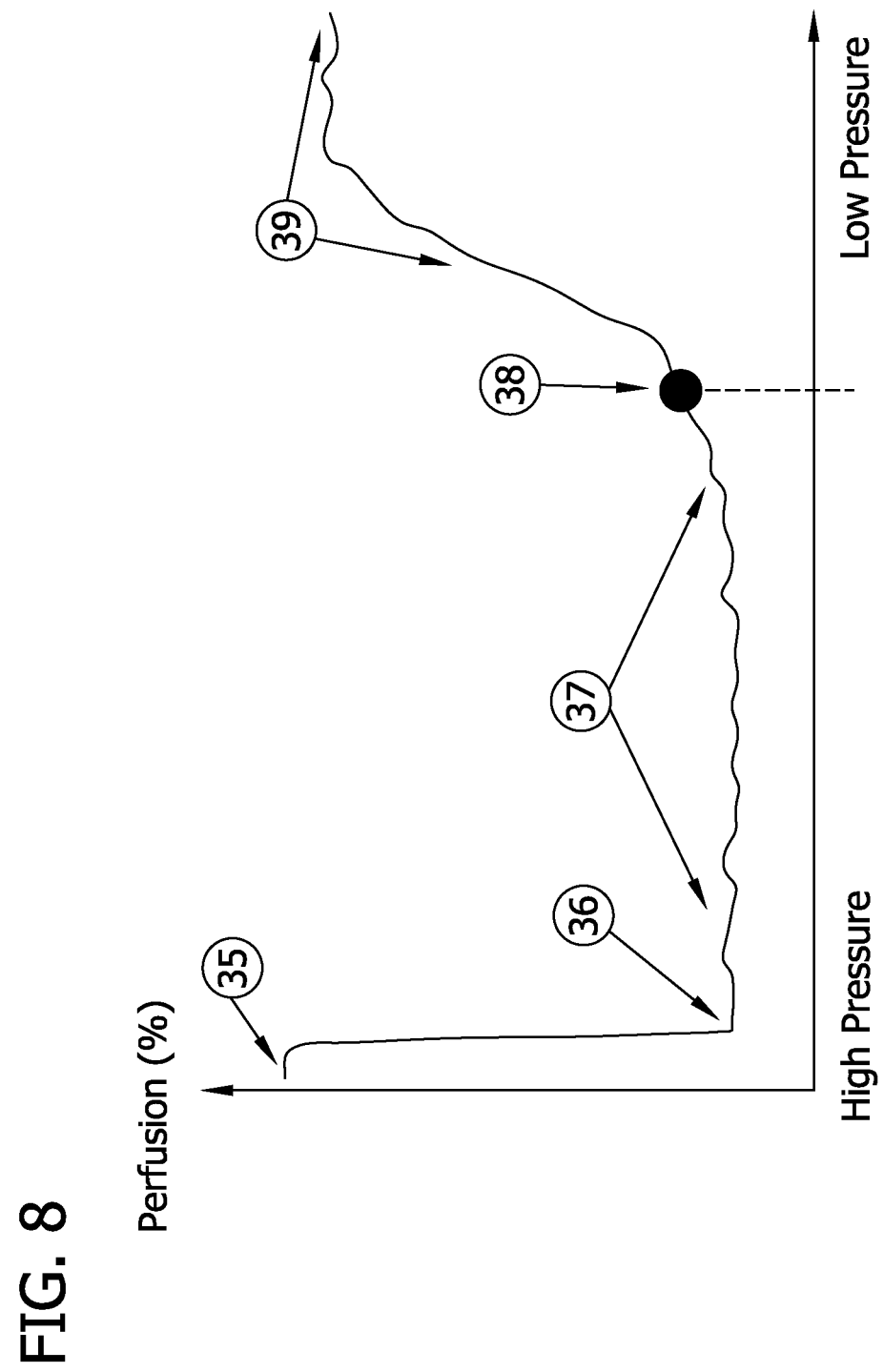
FIG. 8 is an exemplary graph depicting perfusion data collected by the control device.
Figure 9:
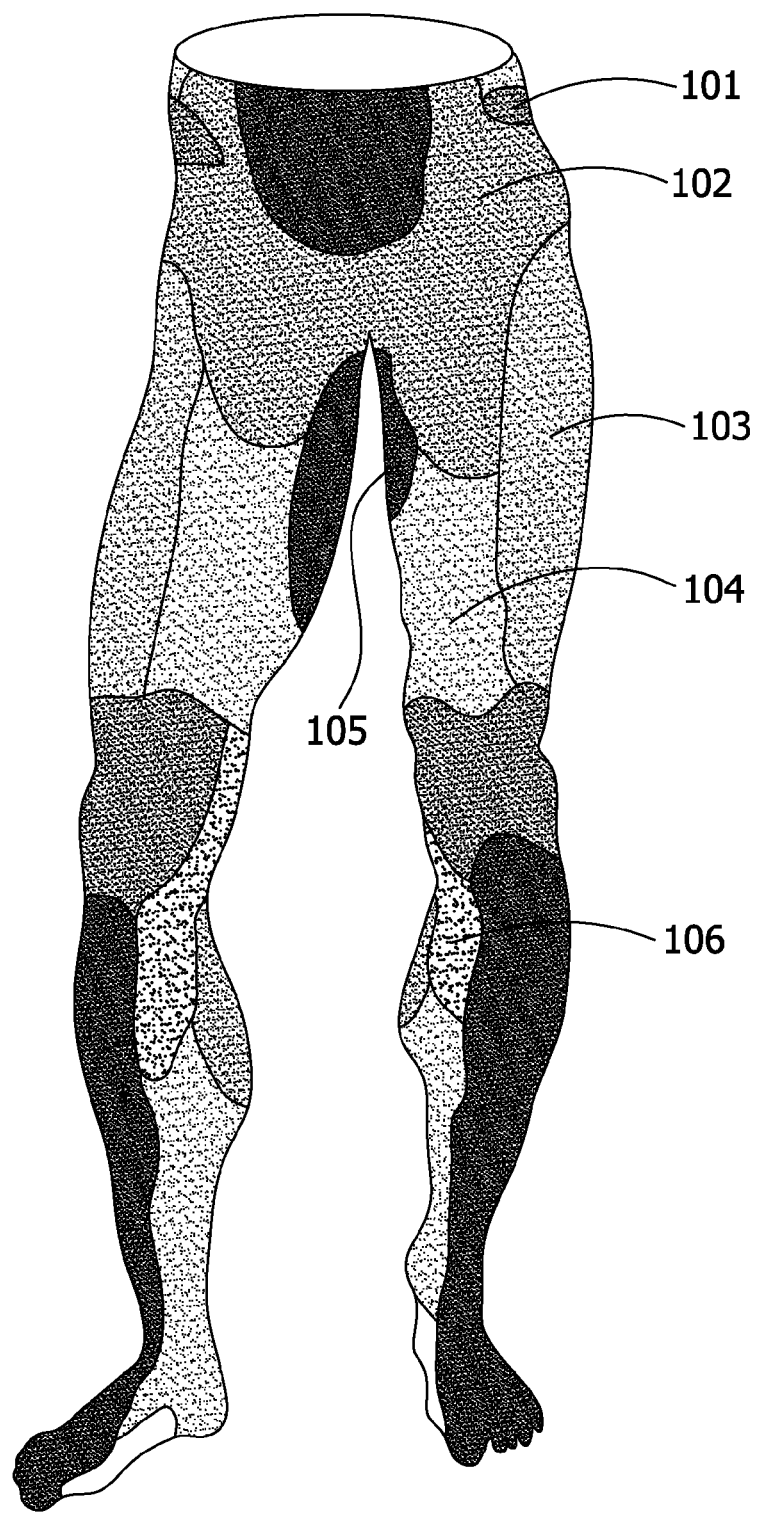
FIG. 9 is a schematic, anterior diagram of the lower body depicting angiosomes.
Figure 10:
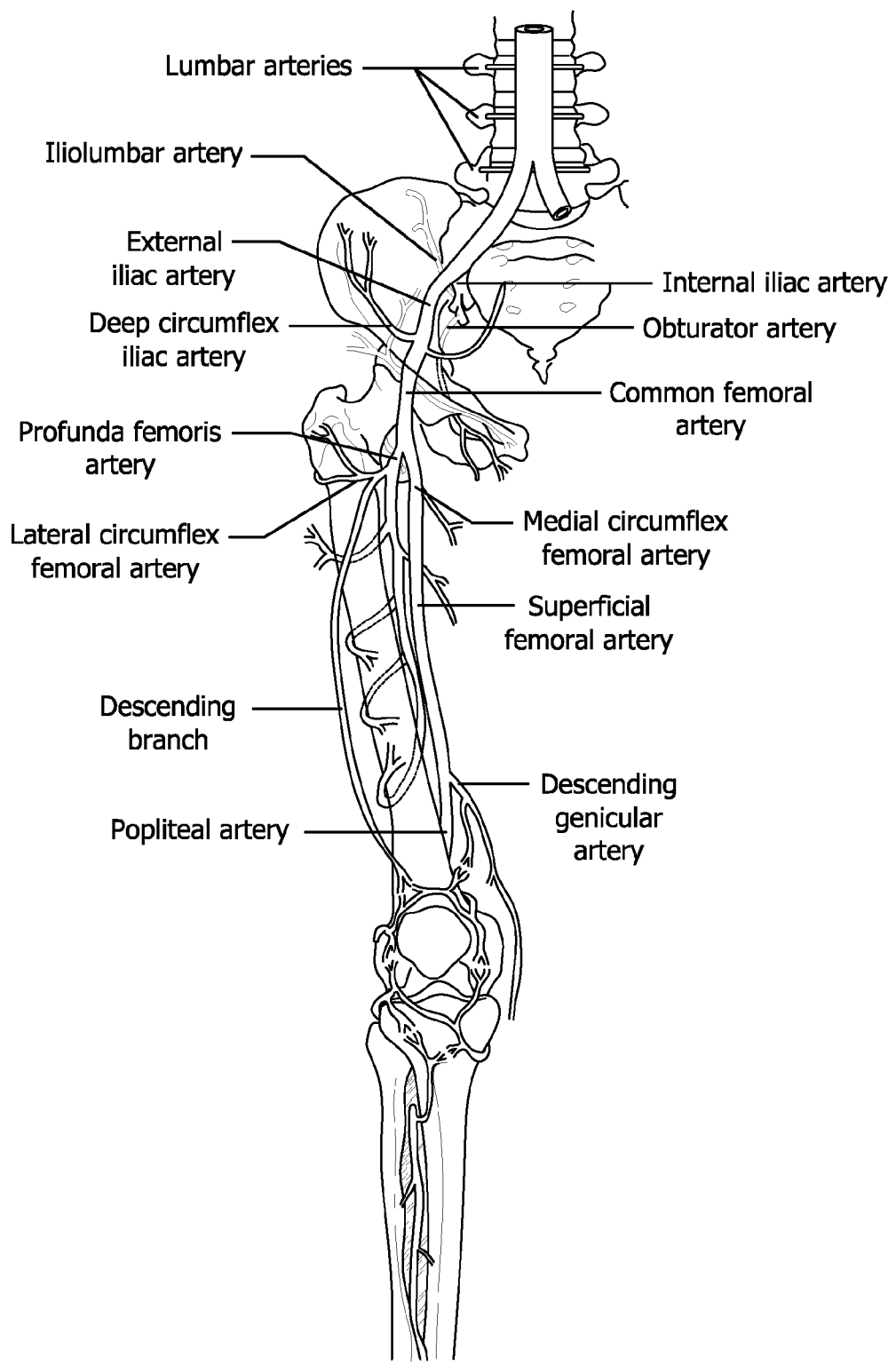
FIG. 10 schematically illustrates the source arteries associated with the angiosomes in FIG. 9.
Figure 11:
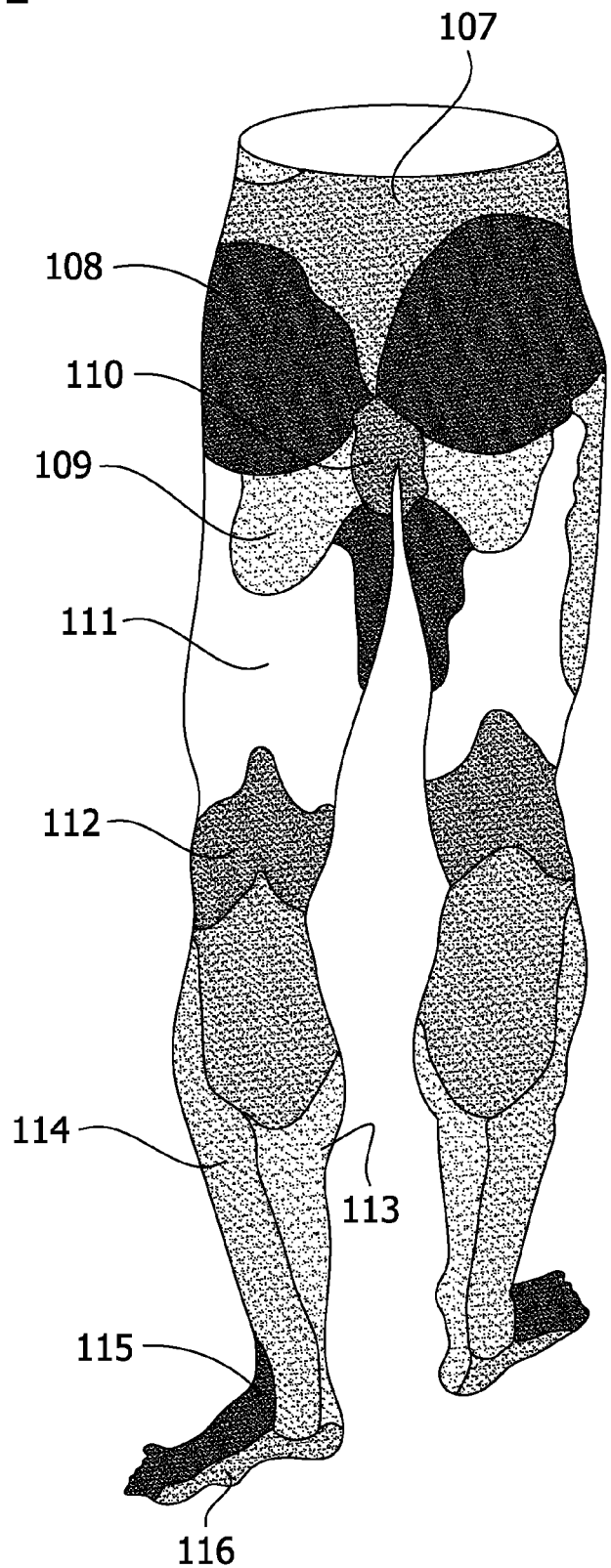
FIG. 11 is a schematic, posterior diagram of the lower body depicting angiosomes.
Figure 12:
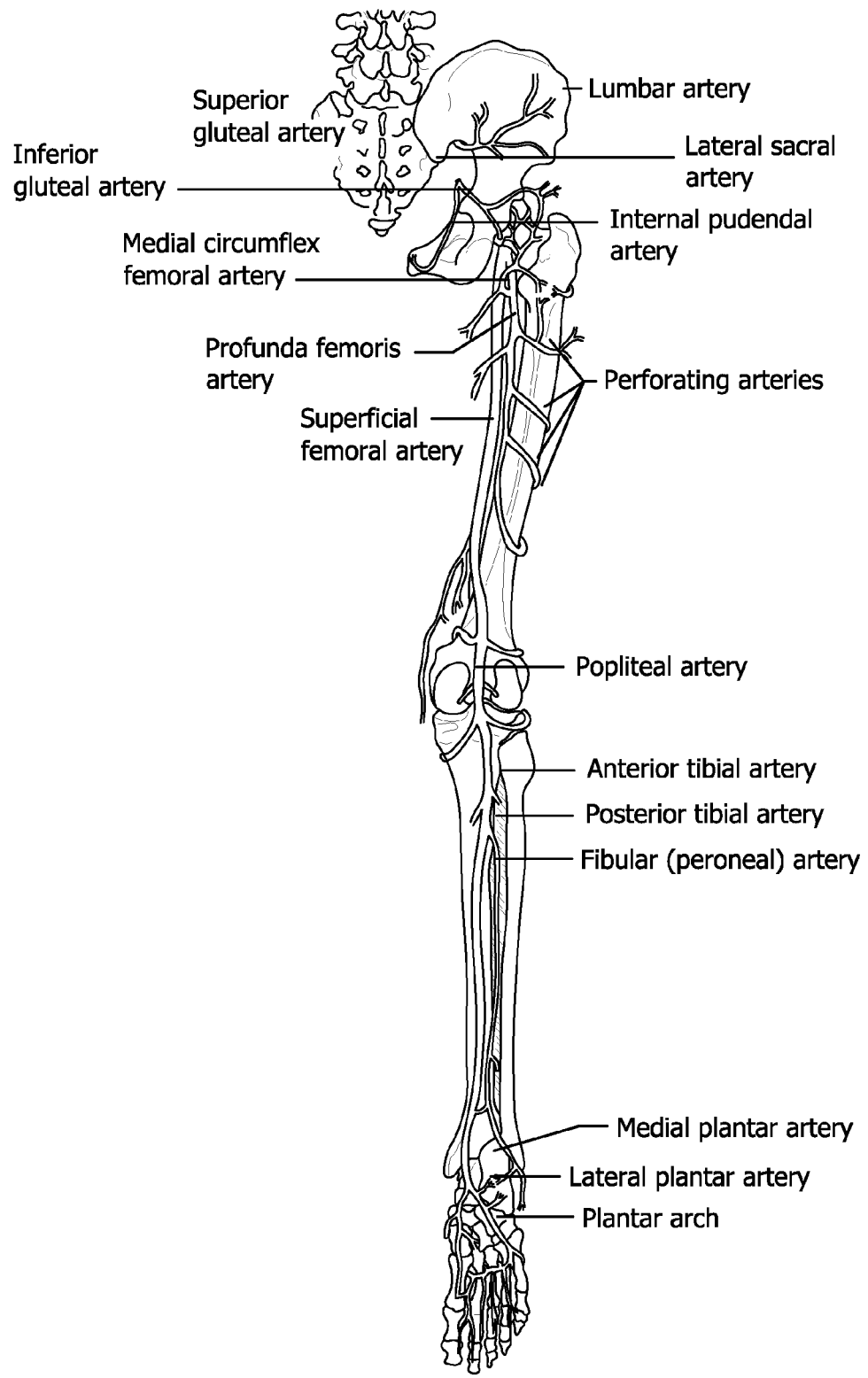
FIG. 12 schematically illustrates the source arteries associated with the angiosomes in FIG. 11.

After (or before) pressurizing the bladders 15a, 15b, 15c to the suitable pressure for the predetermined amount of time, the control circuit 26 receives sensor signals from the perfusion sensors 30. While receiving these signals from the perfusion sensors 30, the control circuit 26 opens the valves to slowly depressurize (e.g., deflate) the bladders at a controlled rate (e.g., 5 mmHg/s). During depressurization, the control circuit 26 receives the sensor signals from the perfusion sensors 30. Exemplary data that may be provided by each of the sensor signals is depicted in FIG. 8 as a graph. Referring to this graph, the sensor signals received from each of the perfusion sensors 30 during (and before) depressurization are indicative of one or more of adequate perfusion 35, no flow 36, baseline flow 37, skin perfusion pressure (SPP) value 38, and return of normal microcirculation 39. Note that point 35 illustrates the condition just before pressure is applied. This exemplary data is provided in U.S. Pat. No. 7,736,311.

The control circuit 26 is programmed to analyze the sensor signal received from each sensor 30 to determine whether there is possible arterial stenosis in the leg being diagnosed. For example, the control circuit 26 may be programmed to determine a possible arterial blockage if the control circuit determines that the skin perfusion pressure (SPP) is below some predetermined threshold value (e.g., 1%). The control circuit 26, alternatively or additionally, may be configured (e.g., programmed) to determine a possible arterial blockage if the control circuit determines that the time elapsed between baseline flow (or some other reference point) and return of normal microcirculation was greater than a threshold value. The control circuit 26 may be programmed to determine a possible arterial blockage in other ways using the sensor signals from each sensor 30.

As set forth above, the control circuit 26 is programmed to map or relate the signal from each sensor 30 to an artery of the leg that corresponds to the angiosome being monitored by the particular sensor. In general, the location of the sensor 30 on the compression device 12 will determine the angiosome to which the sensor is monitoring, which in turn, relates to a particular artery. This determination is made based on anatomy and the projected location of the sensor 30 on the leg when the compression device 12 is donned. In one embodiment, the axial position of each sensor 30 along a given row of perfusion sensors can help determine the location of a possible stenosis along the length of the associated artery. For example, in the illustrated embodiment (FIG. 2) the sensors 30 are grouped into 7 groups (groups A1-A7) based on the respective angiosomes being monitored. Thus, the sensors 30 in group 1 are sensing capillary beds relating to the same angiosome A1, the sensors in group 2 are sensing capillary beds relating to the same angiosome A2 that is different than angiosome A1, and so on. Although FIGS. 1 and 2 do not depict precise groupings of the sensors 30, in general the sensors 30 in groups A1, A4 and A7 relate to the angiosome that is supplied blood by the femerol artery; the sensors in groups A2, A5, and A8 relate to the angiosome that is supplied blood by the profunda artery; and the sensors in groups A3, A6 and A9 relate to the angiosome that is supplied by the popliteal artery. In other embodiments, additional groups may relate to the angiosomes that are supplied by the respective anterior tibial artery, the posterior tibial artery, and the peroneal artery.

In one embodiment, the control circuit 26 may determine the artery of the leg that corresponds to each sensor 30 based on information provided by the sensor in the sensor signal. As an example, each sensor 30 may configured to send an identifier signal (e.g., within the sensor signal) that identifies the angiosome or location on the compression sleeve that corresponds to the sensor. In another example, the identifier signal may identify the sensor 30, and the control circuit 26 may be programmed to determine the location of the sensor based on the sensor identifier. The control circuit 26 may be capable of mapping the each sensor 30 to one or more angiosomes in other ways without departing from the scope of the present invention.

In general, by mapping each sensor 30 to a particular artery, based on the locations of angiosomes, the control circuit 26 is programmed to identify the artery that is likely occluded (partially or totally) and causing a measured, decreased skin perfusion. In this way, the perfusion monitoring system 10 provides diagnosis of peripheral artery disease, including identification of particular arteries that are occluded (partially or totally) and causing the decreased skin perfusion, without using medical imaging to produce an angiogram. In particular, if the control circuit 26 determines that a sensor signal from a particular sensor 30 is indicative of possible peripheral artery disease, the control circuit 26 then identifies the artery that supplies blood to the angiosome (or area) that is being monitored by the particular sensor. In one embodiment, when the control circuit 26 identifies an artery that potentially has an occlusion (partial or total), this information is communicated to the practitioner (or user) via a graphical user interface on a user interface display (e.g., LCD and/or touch screen) 40 of the control device 14. In one non-limiting example, the control circuit may 26 be programmed to generate the name of the artery that possibly has a blockage on the user interface display 40. In another non-limiting example, the control circuit 26 may be programmed to generate a graphical rendering of the leg (or other body portion), including the main arteries, and identify the location of the artery that is possibly occluded (including the name of the artery) and/or identify the location of the angiosome corresponding to the location of the sensor 30 from which the data used to make the assessment originated (including the name of the angiosome). Identification of the location of the sensor 30, relative to the compression device 12, from which the data used to make the assessment originated may also be generated on the user interface display 40. In another non-limiting example, the control circuit 26 may be programmed to also communicate to the user the artery (or arteries) and/or angiosome (or angiosomes) that were not determined to have possible blockage. The user interface 40 for communicating the diagnosis may be separate from a user interface for controlling operation of the control device 14, or the user interfaces may be the same.

Figure 5:
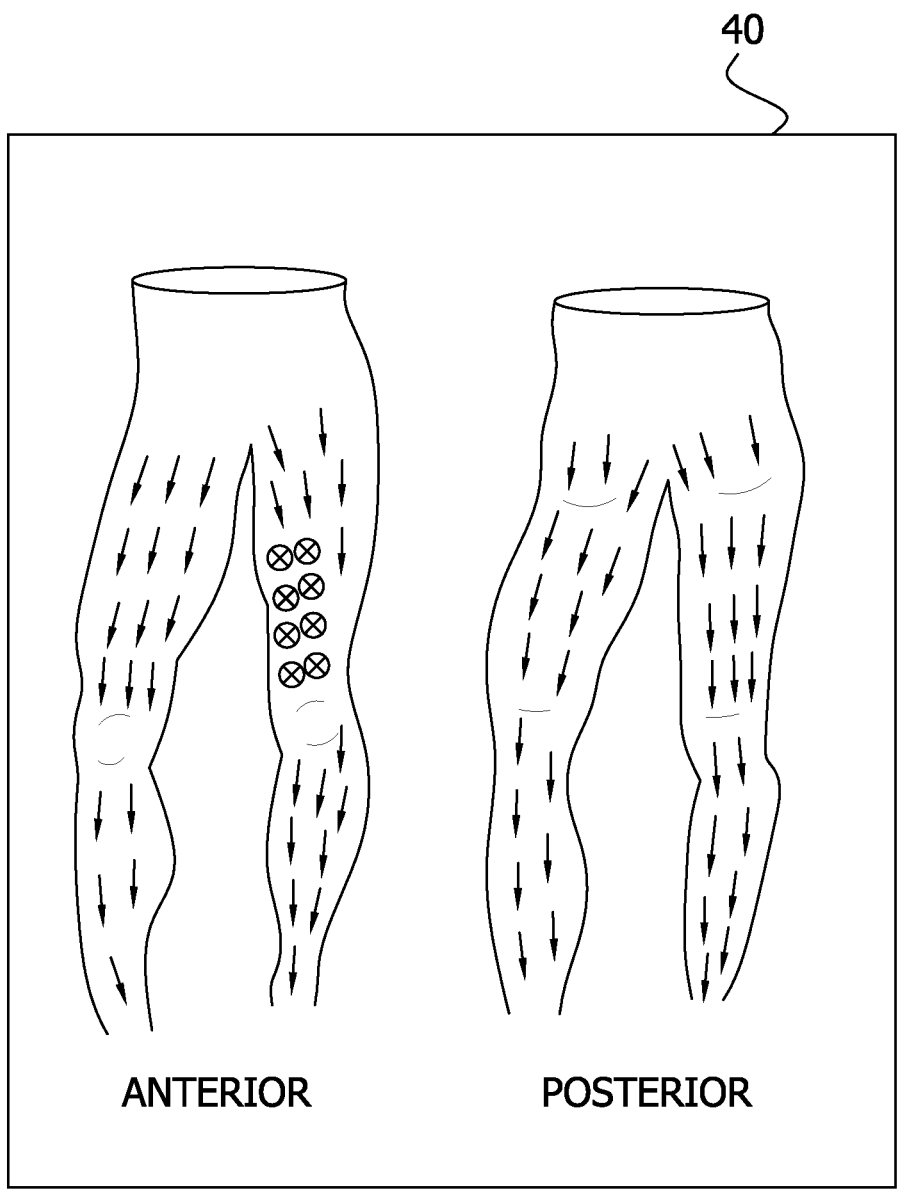
FIGS. 5-7 are an exemplary, schematic screen shots of a graphical user interface during a second mode of operation of the monitoring system, the graphical user interface depicting the revascularization of the leg.
Figure 6:
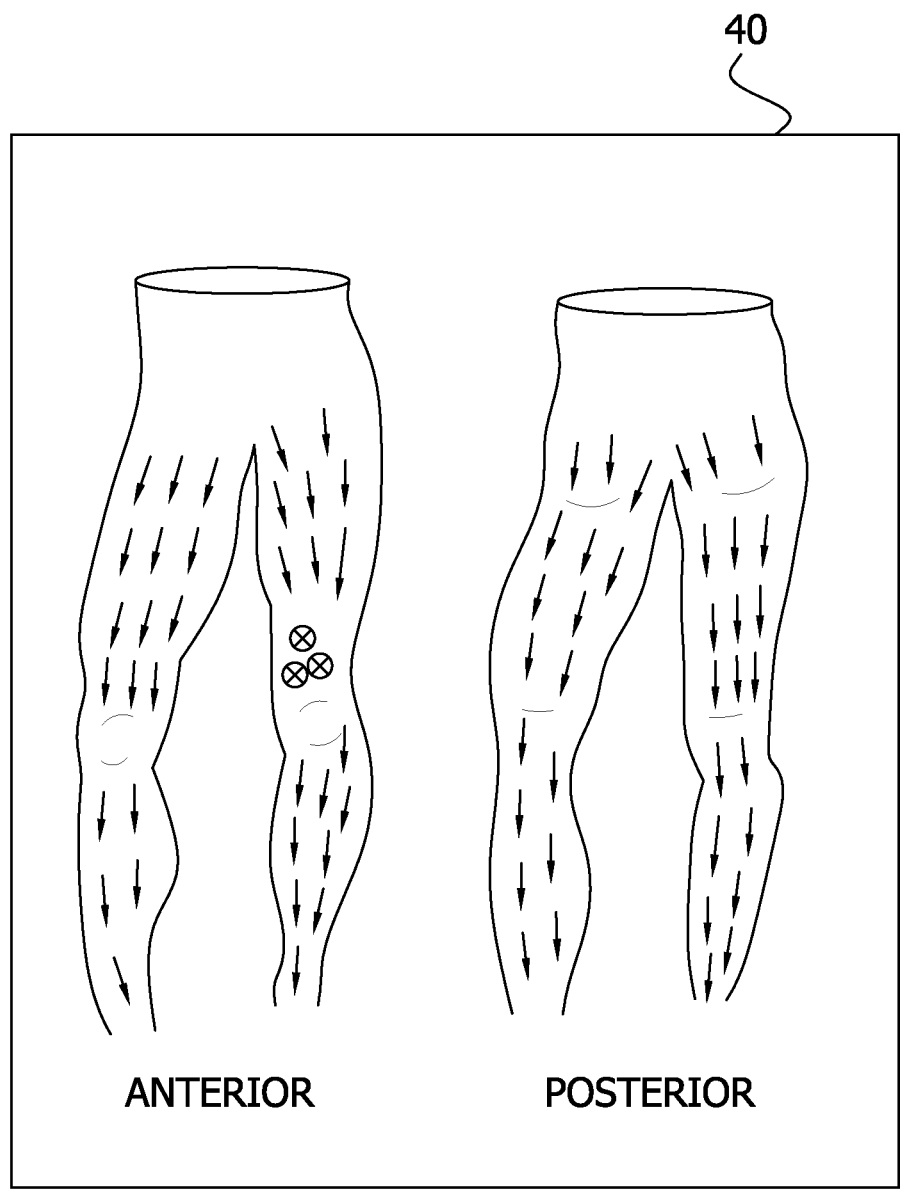
Figure 7:
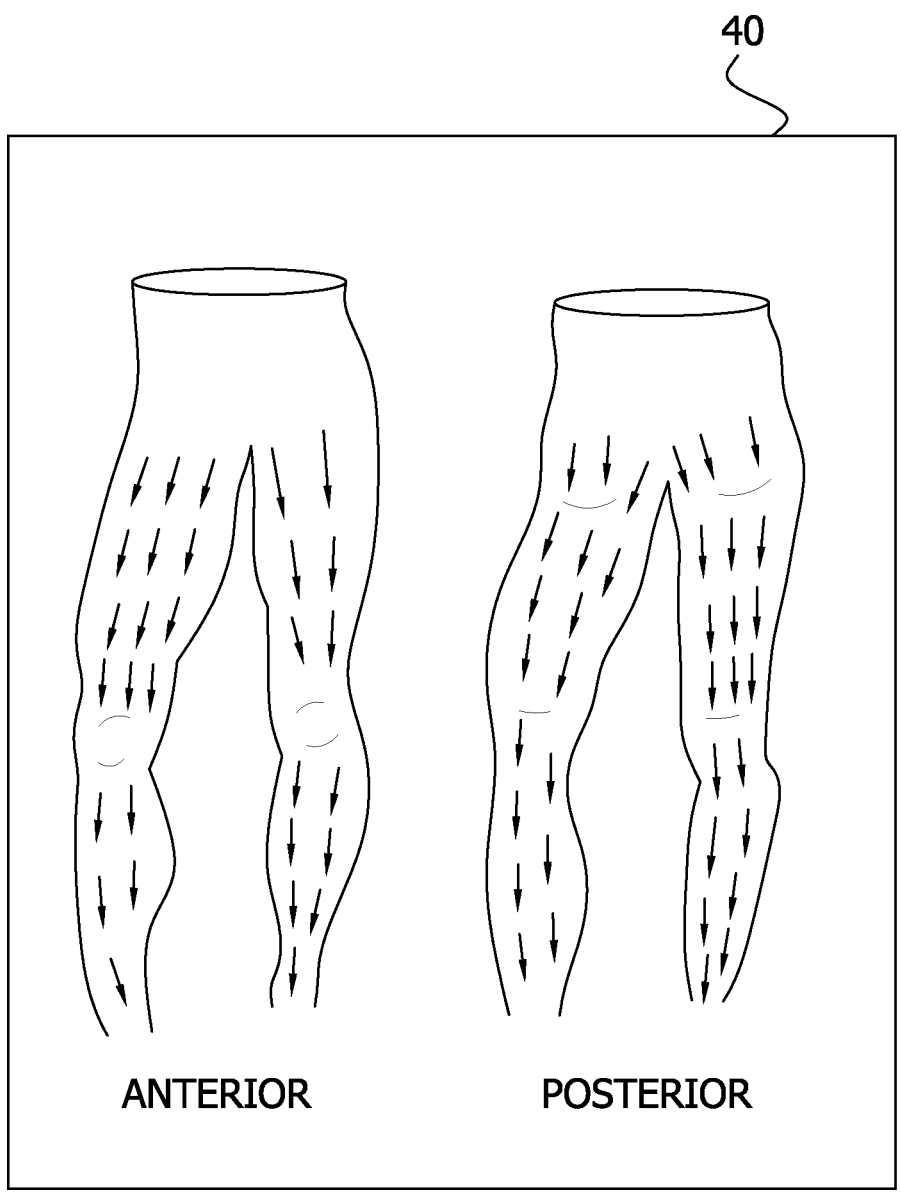

Referring to FIGS. 5-7, in another mode of operation (i.e., a treatment monitoring mode) the perfusion monitoring system 10 may be used during revascularization procedure to monitor the progress of revascularizing one or more regions of the leg or other body part. This process is similar to process of diagnosing peripheral artery disease and identifying one or more arteries that may have blockage, except that the control circuit 26 does not necessarily map the sensors 30 to specific angiosomes and/or arteries to communicate the artery (or arteries) that are potentially blocked. Instead, the control circuit 26 maps the sensors 30 to areas of the legs and generates a graphic representation of the leg to indicate areas of the leg that have adequate perfusion and areas of the leg that do not have adequate perfusion. For example, in FIGS. 5-7 the arrows indicate adequate perfusion, while the X's indicate less than adequate perfusion, although other ways of communicating such information is within the scope of the present invention. It is envisioned that in this mode of operation, the practitioner (or user) is aware of the location of the blockage site and is actively treating the blockage, such as by an atherectomy procedure, while monitoring revascularization on the user interface display 40. Thus, in this mode the perfusion monitoring system 10 provides the practitioner with a means to determine when revascularization (or increased revascularization) has occurred (FIG. 7), and thus, determine when/if treatment is successful.

In one embodiment, the perfusion monitoring system 10 is capable of operating in both of the above described modes (e.g., a diagnostic mode and a treatment monitoring mode), although it may have only one mode or other modes. In one example, the perfusion monitoring system 10 includes an input 50 (e.g., a button or an icon on a touch screen user interface display 40) to allow the user to select between at least the diagnostic mode and the treatment mode. It is also envisioned that during operation of the perfusion monitoring system 10, the control circuit 26 is programmed to generate additional graphical user interfaces on the user interface display 40. For example, the control circuit 26 may be programmed to generate the graph shown in FIG. 8 on the user interface display 40. The control circuit 26 may be configured to generate additional user graphical user interfaces on the user interface display 40. In one example (FIG. 1), an input 45 (e.g., a button or icon on a touch screen user interface display 40) on the perfusion monitoring system 10 allows the user to selectively switch between graphical user interfaces on the interface display.

The perfusion monitoring system 10 is advantageous in monitoring peripheral artery disease. If the device is used during a PAD intervention, progress of the treatment can be monitored independently of a standard angiogram. This will reduce the amount of radiation clinicians and patients are subjected to, as well as reducing the amount of contrast media which must be administered to the patient. The reduction of contrast media is beneficial, especially for those patients who are renally compromised such as diabetics. It may be possible to objectively measure procedural success using the device, rather than relying on a subjective angiogram as a measure of success. This may result in shorter procedure times by preventing a clinician from unnecessarily over treating a patient such as during an atherectomy treatment by removing plaque burden that does not contribute to disease symptoms, or by preventing the treatment of lesions that are not contributing to disease symptoms. Another benefit of using the device during an interventional procedure is that it would be possible to detect embolic events, again independently of angiography. The device may be able to detect embolic events that are not detected by angiography by detecting skin perfusion changes caused by arteries that are too small to be noticed on an angiogram, or were not perfused well enough on the initial angiogram to be detected by the clinician.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An angiosome-based perfusion monitoring system for peripheral artery disease, the monitoring system comprising:
   a compression device sized and shaped for placement on a limb of a subject, the compression device including:
   a plurality of pressurizable bladders configured to exert a suitable compressive force on the limb of the subject when pressurized to substantially occlude blood flow into skin capillary beds adjacent to the plurality of pressurizable bladders, and
   a plurality of spaced apart perfusion sensors, wherein each sensor of the plurality of perfusion sensors is located generally adjacent at least one bladder of the plurality of pressurizable bladders, each perfusion sensor configured to detect a perfusion parameter of skin capillary beds adjacent the perfusion sensor for quantifying skin capillary bed perfusion and generate a signal indicative of the perfusion parameter,
   wherein at least one sensor of the plurality of perfusion sensors is a first-angiosome sensor for detecting the perfusion parameter of a skin capillary bed in a first angiosome of the limb and at least one sensor of the plurality of perfusion sensors is a second-angiosome sensor for detecting the perfusion parameter of a skin capillary bed in a second angiosome of the limb that is different from the first angiosome, the first-angiosome sensor located generally adjacent a first bladder of the plurality of pressurizable bladders and the second-angiosome sensor located generally adjacent a second bladder of the plurality of pressurizable bladders that is different from the first bladder.

2. The monitoring system of claim 1, wherein the first-angiosome sensor comprises a plurality of first-angiosome sensors, and wherein the second-angiosome sensor comprises a plurality of second-angiosome sensors.

3. The monitoring system of claim 2, wherein the first-angiosome sensors are arranged in a first row extending across the first bladder, and wherein the second-angiosome sensors are arranged in a second row, different from the first row, extending across the second bladder.

4. The monitoring system of claim 3, wherein the first and second rows are spaced apart along a length of the compression device.

5. The monitoring system of claim 2, wherein the first-angiosome sensors and the second-angiosome sensors are arranged in a same row extending across the first bladder and the second bladder.

6. The monitoring system of claim 1, wherein the plurality of pressurizable bladders are spaced apart along a length of the compression device, and wherein the compression device is sized and shaped for placement on a leg of the subject.

7. The monitoring system of claim 1, wherein the perfusion sensors comprise pulse oximetry sensors.

8. The monitoring system of claim 1, in combination with a control device, the control device comprising:
   a source of pressurized fluid for introducing into the compression device that is placed on the limb of the subject; and
   a control circuit configured to:
   pressurize the first bladder when the compression device is placed on the limb of the subject to substantially occlude blood perfusion in skin capillary beds adjacent to the first bladder, and depressurize the first bladder at a first controlled rate after pressurizing the first bladder,
   pressurize the second bladder when the compression device is placed on the limb of the subject to substantially occlude blood perfusion in skin capillary beds adjacent to the second bladder, and depressurize the second bladder at a second controlled rate after pressurizing the second bladder,
   receive separate sensor signals from the first-angiosome sensor and the second-angiosome sensor during respective depressurization of the first bladder and the second bladder, wherein the sensor signals are indicative of perfusion parameters of skin capillary beds adjacent the first-angiosome sensor and the second-angiosome sensor for quantifying skin capillary bed perfusion,
   map sensor signals from the first-angiosome sensor to at least one of the first angiosome or a first artery of the limb, map sensor signals from the second-angiosome sensor to at least one of the second angiosome or a second artery of the limb different from the first artery of the limb, and determine, for each perfusion sensor, whether the received sensor signals are indicative of peripheral artery disease.

9. The monitoring system of claim 8, wherein each of the sensors is configured to send an identifier signal to the control device identifying the angiosome or location on the compression device corresponding to the sensor, wherein the control device is configured to receive each identifier signal and determine the location of the sensor based on the sensor identifier.

10. The monitoring system of claim 8, wherein the control device is configured to selectively pressurize the first bladder and the second bladder.

11. The monitoring system of claim 8, wherein the first controlled rate and the second controlled rate are the same.

12. The monitoring system of claim 8, wherein the first controlled rate and the second controlled rate are different.

13. The monitoring system of claim 1, further comprising a third-angiosome sensor for detecting the perfusion parameter of a skin capillary bed in a third angiosome of the limb, the third-angiosome sensor located generally adjacent one of the first bladder or the second bladder.

14. An angiosome-based perfusion monitoring system for peripheral artery disease, the monitoring system comprising:
a control device including:
a source of pressurized fluid for introducing into a compression device that is placed on a limb of a subject; and
a control circuit configured to:
pressurize a first bladder of a plurality of pressurizable bladders of a compression device when the compression device is placed on a limb of a subject to substantially occlude blood perfusion in skin capillary beds adjacent to the first bladder, and depressurize the first bladder at a first controlled rate after pressurizing the first bladder,
pressurize a second bladder of the plurality of pressurizable bladders when the compression device is placed on the limb of the subject to substantially occlude blood perfusion in skin capillary beds adjacent to the second bladder, the second bladder being different from the first bladder, and depressurize the second bladder at a second controlled rate after pressurizing the second bladder,
receive separate sensor signals from a plurality of perfusion sensors of the compression device during respective depressurization of the first bladder and the second bladder, wherein each sensor of the plurality of perfusion sensors is located generally adjacent at least one bladder of the plurality of pressurizable bladders, and wherein the sensor signals are indicative of perfusion parameters of skin capillary beds adjacent the perfusion sensors for quantifying skin capillary bed perfusion,
map sensor signals from a first sensor of the plurality of perfusion sensors to at least one of a first angiosome or a first artery of the limb, the first sensor located generally adjacent the first bladder,
map sensor signals from a second sensor of the plurality of perfusion sensors to at least one of a second angiosome or a second artery of the limb, the second sensor located generally adjacent the second bladder, wherein the second angiosome and second artery are different from the first angiosome and the first artery, respectively, and determine, for each perfusion sensor, whether the received sensor signals are indicative of peripheral artery disease.

15. The monitoring system of claim 14, wherein the control device is configured to determine at least one of: adequate perfusion, no flow, baseline flow, skin perfusion pressure value, and return of microcirculation based on the received sensor signals.

16. The monitoring system of claim 15, wherein the control device is configured to determine the skin perfusion pressure value based on the received sensor signals and compare the skin perfusion pressure value to a threshold value to determine whether the received sensor signals are indicative of peripheral artery disease.

17. The monitoring system of claim 15, wherein the control device is configured to determine the baseline flow and the return of microcirculation based on the received sensor signals and determine a time elapsed between the baseline flow and the return of microcirculation to determine whether the received sensor signals are indicative of peripheral artery disease.

18. The monitoring system of claim 14, wherein the control device comprises a user interface display, wherein the control circuit is configured to generate a graphical rendering of the limb and identify on the graphical rendering the location of a determined peripheral artery disease.

19. The monitoring system of claim 14, wherein the control device is configured to selectively pressurize the first bladder and the second bladder.

20. A method of monitoring for peripheral artery disease, the method comprising:
pressurizing a first bladder of a plurality of pressurizable bladders of a compression device that is placed on a limb of a wearer so as to substantially occlude blood perfusion to skin capillary beds adjacent the first bladder;
depressurizing the first bladder at a first controlled rate after pressurizing the first bladder;
pressurizing a second bladder of the plurality of pressurizable bladders of the compression device that is placed on the limb of the wearer so as to substantially occlude blood perfusion to skin capillary beds adjacent the second bladder, the second bladder being different from the first bladder;
depressurizing the second bladder at a second controlled rate after pressurizing the second bladder;
detecting, during the depressurizing of the first bladder and using a first perfusion sensor of the compression device, a perfusion parameter of a skin capillary bed located in a first angiosome of the limb, the first perfusion sensor being located generally adjacent the first bladder;
generating a first sensor signal indicative of the perfusion parameter detected by the first perfusion sensor;
detecting, during the depressurizing of the second bladder and using a second perfusion sensor of the compression device, a perfusion parameter of a skin capillary bed located in a second angiosome of the limb that is different from the first angiosome of the limb, the second perfusion sensor being located generally adjacent the second bladder;
generating a second sensor signal indicative of the perfusion parameter detected by the second perfusion sensor;

receiving, by a control circuit, the first and second sensor signals;

mapping, by the control circuit, the first sensor signal to at least one of the first angiosome and a first artery associated with the first angiosome;

mapping, by the control circuit, the second sensor signal at least one of the second angiosome and a second artery associated with the second angiosome; and determining, by the control circuit, whether the first and second sensor signals are indicative of peripheral artery disease.

21. The method of claim 20, further comprising determining, by the control circuit, at least one of: adequate perfusion, no flow, baseline flow, skin perfusion pressure value, and return of microcirculation based on the received sensor signals.

22. The method of claim 21, further comprising determining, by the control circuit, the skin perfusion pressure value based on the received sensor signals and comparing the skin perfusion pressure value to a threshold value to determine whether the received sensor signals are indicative of peripheral artery disease.

23. The method of claim 21, further comprising determining, by the control circuit, the baseline flow and the return of microcirculation based on the received sensor signals, and calculating, by the control circuit, a time elapsed between the baseline flow and the return of microcirculation for use in determining whether the received sensor signals are indicative of peripheral artery disease.

24. The method of claim 21, further comprising generating, by the control circuit, a graphical rendering of the limb, and identifying, by the control circuit, the location of the determined peripheral artery disease on the graphical rendering.

25. The method of claim 20, further comprising detecting, during depressurizing one of the first bladder or the second bladder and using a third perfusion sensor of the compression device, a perfusion parameter of a skin capillary bed located in a third angiosome of the limb that is different from the first angiosome and the second angiosome, the third perfusion sensor being located generally adjacent one of the first bladder or the second bladder.

26. The method of claim 20, wherein the first controlled rate and the second controlled rate are the same.

27. The method of claim 20, wherein the first controlled rate and the second controlled rate are different.

* * * * *